(12) United States Patent
Hong et al.

(10) Patent No.: US 10,414,710 B1
(45) Date of Patent: Sep. 17, 2019

(54) METHOD FOR MANUFACTURING ADIPIC ACID USING BIOMASS

(71) Applicants: HYUNDAI MOTOR COMPANY, Seoul (KR); KIA MOTORS CORPORATION, Seoul (KR); SEOUL NATIONAL UNIVERSITY R&DB FOUNDATION, Seoul (KR)

(72) Inventors: Chae-Hwan Hong, Seoul (KR); Ha-Eun Jeong, Yongin-si (KR); Na-Kyong Yun, Suwon-si (KR); Sung-Wan Jeon, Suwon-si (KR); So-Hyun Kwon, Seoul (KR); Na-Ra Shin, Seoul (KR); So-Jeong Moon, Seoul (KR); Young-Gyu Kim, Gunpo-si (KR)

(73) Assignees: Hyundai Motor Company, Seoul (KR); Kia Motors Corporation, Seoul (KR); Seoul National University R&DB Foundation, Seoul (KR)

( * ) Notice: Subject to any disclaimer, the term of this patent is extended or adjusted under 35 U.S.C. 154(b) by 0 days.

(21) Appl. No.: 16/151,647

(22) Filed: Oct. 4, 2018

(30) Foreign Application Priority Data

Aug. 28, 2018 (KR) ........................ 10-2018-0101431

(51) Int. Cl.
| | | |
|---|---|---|
| *C07C 51/06* | (2006.01) | |
| *C07C 51/377* | (2006.01) | |
| *B01J 23/42* | (2006.01) | |
| *C07C 231/12* | (2006.01) | |
| *C07C 233/01* | (2006.01) | |
| *C07C 55/14* | (2006.01) | |

(52) U.S. Cl.
CPC ............... *C07C 51/06* (2013.01); *B01J 23/42* (2013.01); *C07C 51/377* (2013.01); *C07C 231/12* (2013.01); *C07C 55/14* (2013.01); *C07C 233/01* (2013.01)

(58) Field of Classification Search
CPC ..... C07C 51/06; C07C 231/12; C07C 51/377; C07C 55/14; C07C 233/01; B01J 23/42
See application file for complete search history.

(56) References Cited

U.S. PATENT DOCUMENTS

2010/0317823 A1* 12/2010 Boussie ................... B01J 23/40
528/323

* cited by examiner

*Primary Examiner* — Yevgeny Valenrod
*Assistant Examiner* — Blaine G Doletski
(74) *Attorney, Agent, or Firm* — Morgan, Lewis & Bockius LLP (57) ABSTRACT

A method for preparing bio adipic acid includes steps of (a) preparing a glucaric acid potassium salt by mixing and reacting glucose, nitric acid ($HNO_3$), sodium nitrite ($NaNO_2$) and potassium hydroxide (KOH), (b) preparing glucamide from the glucaric acid potassium salt prepared in the step (a), (c) preparing 2,4-hexadiene diamide by performing a deoxydehydration reaction on the glucamide prepared in the step (b), (d) preparing adipamide by introducing the 2,4-hexadiene diamide prepared in the step (c), hydrogen and a hydrogenation catalyst to a reactor and performing a hydrogenation reaction, and (e) preparing adipic acid by introducing the adipamide prepared in the step (d) and an aqueous hydrochloric acid solution to a reactor and then performing a hydrolysis reaction at a specific temperature.

18 Claims, 7 Drawing Sheets

METHOD FOR MANUFACTURING ADIPIC ACID USING BIOMASS

CROSS REFERENCE

This patent application claims the benefit of Korean Patent Application No. 10-2018-0101431, filed on Aug. 28, 2018, the entire content is hereby incorporated by reference.

BACKGROUND

Field

The present disclosure relates to a novel method for manufacturing adipic acid, which is diversely used as a raw material of nylon and the like for automotive engine chassis injection molding components, from glucose derived from biomass, and in particular, to a method for manufacturing adipic acid by preparing a glucaric acid potassium salt from glucose derived from plant resources on land as biomass, preparing glucamide from the prepared glucaric acid potassium salt, and then preparing adipic acid from 2,4-hexadiene diamide prepared through a deoxydehydration (DODH) reaction thereafter.

Description of Related Art

Studies on technologies of manufacturing biomaterials and chemical materials through various methods using biomass derived from plant resources such as corn, sugar cane, woody plant resources, palm or seaweed as future resources capable of replacing petroleum resources that have been used as raw materials in automotive component and material businesses progressed around the world.

Materials of interior and exterior injection molding components currently used in automobiles include polypropylene, nylon, polycarbonate, acrylonitrile butadiene styrene (ABS) materials and the like. Among these, polypropylene materials have been used the most quantitatively, and nylon materials as the second most quantitatively used are used in approximately 15 kg per one automobile. Accordingly, substantial ripple effects may be expected when changing such a highly utilized nylon-manufacturing technology to a biomass-based. Actually, studies on biomass-based nylon materials have been actively progressed currently.

Among various nylon materials, demands for nylon 66, a typical nylon material together with nylon 6, are high due to its excellent properties, however, process technologies producing nylon 66 using biomass as a raw material have not been established yet. Accordingly, development of processes for producing bio nylon 66 may expect striking ripple effects in environmental aspects as well as in economic aspects.

Nylon 66 has excellent heat resistance, abrasion resistance and chemical resistance, and is used in components requiring high temperature properties among automotive components, and used in second to the most after nylon 6 among nylon materials used in automotive components. In addition, nylon 66 is manufactured by a dehydration polymerization reaction of hexamethylene diamine and adipic acid, and the adipic acid used as a monomer is currently produced starting from crude oil and through a chemical synthesis process with intermediates starting from benzene obtained in a crude oil purification process to cyclohexanone.

However, this technology of manufacturing process causes problems such as oil price instability, using benzene that is a toxic material, and producing environmental polluting byproducts including nitric oxide ($NO_x$), and is in need of being replaced to a bio process technology. Accordingly, nylon production using a bio process may induce effects of both reducing raw material dependence on petroleum and reducing the generation of environmental pollutants.

In developing a bio process of nylon 66, a technology of synthesizing and manufacturing adipic acid, a monomer of nylon 66, from biomass is considered to be the most important.

As a technology of a U.S. company, RENNOVIA INC., of manufacturing adipic acid using glucose, U.S. Patent Application Laid-Open Publication No. 2010-0317823 was disclosed. However, such a process prepares glucaric acid from glucose, and prepares adipic acid after that by processing a follow-up reaction at a high temperature and a high pressure. Since the glucaric acid produced as an oxidation reaction material of glucose in the manufacturing process tends to form a ring structure due to instability of the structure itself, there are problems in that process stability of the follow-up process carried out for manufacturing adipic acid decreases, and production efficiency decreases as well.

SUMMARY OF THE INVENTION

In view of the above, an embodiment of the present invention is directed to providing a method for manufacturing adipic acid from biomass, an environmental-friendly material, by preparing a glucaric acid potassium salt from glucose derived from plant resources, preparing glucamide from the prepared glucaric acid potassium salt, then preparing 2,4-hexadiene diamide through a deoxydehydration (hereinafter, also referred to as 'DODH') reaction, and then preparing the adipic acid through a hydrogenation reaction and a hydrolysis process. This aims to develop a more stable and efficient process compared to methods used in the art.

Other objects and advantages of the present invention can be understood by the following description, and become apparent with reference to the embodiments of the present invention. Also, it is obvious to those skilled in the art to which the present invention pertains that the objects and advantages of the present invention can be realized by the means as claimed and combinations thereof.

In accordance with an embodiment of the present invention, a method for manufacturing adipic acid of the prevent invention includes step (a) preparing a glucaric acid potassium salt by mixing and reacting glucose, nitric acid ($HNO_3$), sodium nitrite ($NaNO_2$) and potassium hydroxide (KOH), step (b) preparing glucamide from the glucaric acid potassium salt prepared in the step (a), step (c) preparing 2,4-hexadiene diamide by performing a deoxydehydration (DODH) reaction on the glucamide prepared in the step (b), step (d) preparing adipamide by introducing the 2,4-hexadiene diamide prepared in the step (c), hydrogen and a hydrogenation catalyst to a reactor and performing a hydrogenation reaction, and step (e) preparing adipic acid by introducing the adipamide prepared in the step (d) and an aqueous hydrochloric acid solution to a reactor and then performing a hydrolysis reaction at a specific temperature.

Specifically, the step (a) may include preparing a reactant by introducing sodium nitrite ($NaNO_2$) to a mixture mixing glucose and nitric acid ($HNO_3$) and then reacting the result at a specific temperature, preparing a basic reactant in a pH value in a range from 9 to 10 by adding potassium hydroxide (KOH) to the reactant, preparing an acidic reactant in a pH value in a range from 3 to 4 by adding nitric acid ($HNO_3$)

to the basic reactant, and obtaining a glucaric acid potassium salt by filtering and washing precipitates formed through aging the acidic reactant.

In the step (a), the preparing of a reactant may be carried out at a reaction temperature of 40° C. to 60° C.

Herein, when the reaction temperature is lower than 40° C., reactivity is low since the reaction temperature does not reach a temperature required for carrying out the reaction, and when the temperature is higher than 60° C., unnecessary byproducts are produced and fail to produce effects such as a yield increase, and therefore, the reaction temperature condition satisfying the above-mentioned range is preferred.

In addition, in the step (a), the sodium nitrite ($NaNO_2$) and the glucose are preferably mixed in a weight ratio in a range from 1:500 to 1:1500, and more preferably, the sodium nitrite ($NaNO_2$) and the glucose may be mixed in a weight ratio of 1:1000.

Herein, the sodium nitrite ($NaNO_2$) is a material inducing crystallization of the glucaric acid potassium salt, and when the ratio is outside the mixing ratio provided above, crystals of the glucaric acid potassium salt, the intended product in the step (a), are not properly produced, and therefore, the mixing ratio satisfying the mixing ratio of the sodium nitrite ($NaNO_2$) and the glucose provided above is preferred.

The step (b) may include removing of potassium from the glucaric acid potassium salt by introducing an acidic solution to a mixture, which is obtained by introducing the glucaric acid potassium salt prepared in the step (a) to a first reaction solvent and mixing the result, and then reacting the result for a specific period of time, and collecting glucamide particles precipitated by adding an aqueous ammonia solution to the material gone through the removing of potassium, mixing the result for a specific period of time, and then adding ethanol thereto.

As the first reaction solvent used in the removing of potassium, any one or more selected from the group consisting of primary alcohols and secondary alcohols having 1 to 10 carbon atoms may be used, however, the most favorable yields are obtained when using methanol, and therefore, using methanol is the most preferred.

As the acidic solution, sulfuric acid ($H_2SO_4$) or para-toluene sulfonic acid may be used.

The removing of potassium is preferably carried out for a reaction time in a range from 12 hours to 24 hours.

As a concentration of the aqueous ammonia solution, a value in a range from 25% by weight to 28% by weight is preferably used.

The step (c) may include preparing a glucamide mixture by introducing the glucamide and a catalyst to a second reaction solvent and mixing the result, and obtaining 2,4-hexadiene diamide formed by performing a deoxydehydration (DODH) reaction through the mixture while being stirred under reflux for a time in a range from 12 hours to 24 hours at a temperature in a range from 120° C. to 150° C.

The second reaction solvent used in the step (c) performs a role of a reducing agent for converting the catalyst to an active state while used as a reaction solvent of the deoxydehydration (DODH) reaction. As such a reaction solvent, any one or more selected from the group consisting of primary alcohols and secondary alcohols having 1 to 10 carbon atoms may be used. Preferably, 1-butanol, 3-pentanol or 1-heptanol may be used, and among these, using 1-butanol is the most preferred.

As the catalyst added to the glucamide mixture, one or more selected from the group consisting of ammonium perrhenate, rhenium oxide ($Re_2O_7$) and $L_xReO_y$, (herein, L=amine, halogen, phenylsilyl, phosphine, alkoxy having 1 to 10 carbon atoms, alkyl having 1 to 10 carbon atoms or COOR (herein, R is alkyl having 1 to 10 carbon atoms), x and y are each independently an integer of 1 to 3, and x+y=7) may be used. Preferably, rhenium oxide ($Re_2O_7$) may be used, and among these, using ammonium perrhenate is preferred.

In the step (d), adipamide may be prepared by introducing hydrogen gas to a reactor with a pressure in a range from 1 bar to 30 bar, introducing the 2,4-hexadiene diamide and a hydrogenation catalyst in a weight ratio in a range from 1:0.05 to 1:0.3, and carrying out a hydrogenation reaction at a temperature in a range from 50° C. to 70° C.

Mixing ratio of the 2,4-hexadiene diamide and the hydrogenation catalyst being less than 1:0.05 in a weight ratio has a disadvantage of declining hydrogenation reaction efficiency, and the mixing ratio being greater than 1:0.3 in a weight ratio has a problem of declining economic feasibility since adipamide production efficiency with respect to the amount of hydrogenation catalyst introduction decreases.

The hydrogenation catalyst is a precious metal catalyst, and specifically, any one or more selected form the group consisting of aluminum, silica, a platinum catalyst supported on a carbon carrier (Pt/C) and a palladium catalyst supported on a carbon carrier (Pd/C) may be used.

Preferably, as the platinum catalyst supported on a carbon carrier (Pt/C) and the palladium catalyst supported on a carbon carrier (Pd/C), those supporting platinum and palladium, precious metals, in 10% by weight on a carbon carrier may be used.

As the aqueous hydrochloric acid solution used in the step (e), a mixture mixing hydrochloric acid and water in a weight ratio in a range from 1:0.05 to 1:0.3 may be used, and a value in a range from 20% by weight to 35% by weight aqueous hydrochloric acid solution may be preferably used.

The step (e) may include evaporating the hydrochloric acid and the water from the hydrolysis reaction-completed reactant, and obtaining adipic acid by introducing acetonitrile to the evaporated reactant as an organic solvent and heating the result.

DESCRIPTION OF SPECIFIC EMBODIMENTS

Hereinafter, each step of a method for manufacturing adipic acid of the present invention will be described in detail with reference to accompanying drawings. However, these are just one embodiment and may be implemented in various different forms by those skilled in the art, and therefore, the scope of the present invention is not limited to the descriptions provided herein.

Meanwhile, terms such as "include" or "add" used in the present specification are not to be construed as being required to include all various constituents or various steps described in the present specification, and need to be construed such that some constituents or some steps among these may not be included, and additional constituents or steps may be further included.

In addition, the number of repetitions of each step, step conditions and the like described in the present invention are not particularly limited as long as it does not depart from goals of the present invention.

In addition, terms such as 'first' and 'second' in the present specification are used to distinguish designated subjects or constituents, and therefore, are not to be limitingly construed in order for specifying certain orders or importance.

Figure 1:
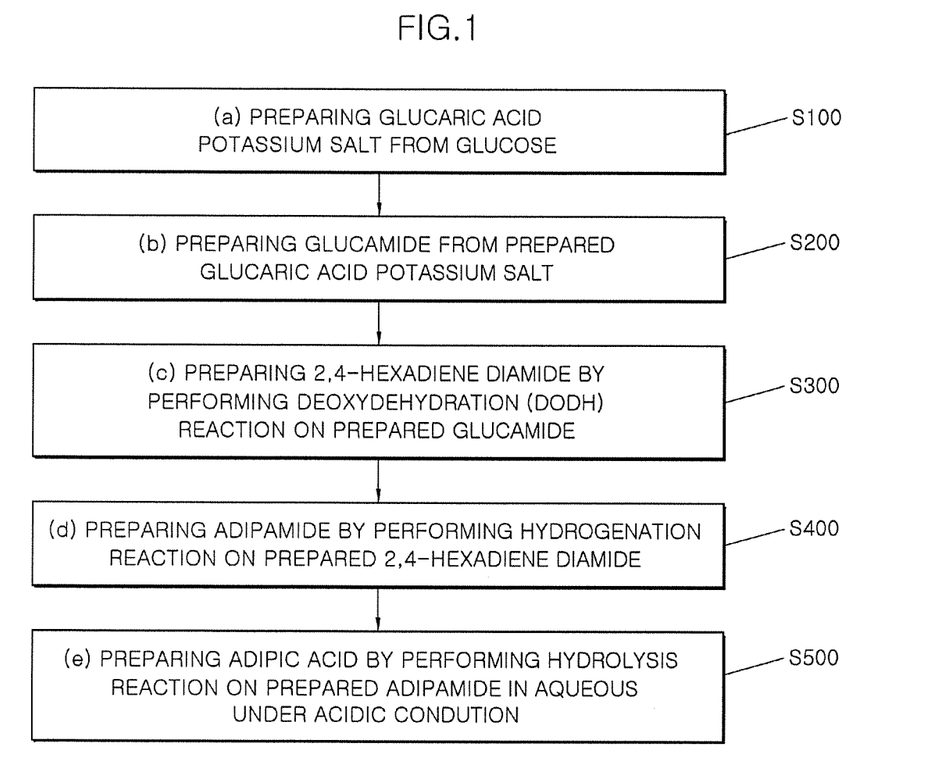
FIG. 1 shows a flow chart of a method for manufacturing adipic acid of the present invention.

As shown in FIG. 1, a method for manufacturing bio adipic acid of the present invention includes step (a) of preparing a glucaric acid potassium salt from glucose (S100), step (b) of preparing glucamide from the prepared glucaric acid potassium salt (S200), step (c) of preparing 2,4-hexadiene diamide by performing a deoxydehydration (DODH) reaction on the prepared glucamide (S300), step (d) of preparing adipamide by performing a hydrogenation reaction on the prepared 2,4-hexadiene diamide (S400), and step (e) of preparing adipic acid by performing a hydrolysis reaction on the prepared adipamide in an aqueous solution under acidic condition (S500).

The preparing of a glucaric acid potassium salt from glucose (S100) prepares a glucaric acid potassium salt from glucose used as a raw material as shown in the following Reaction Formula 1, and as the glucose used herein, glucose derived from plant resources on land as biomass may be preferably used, however, the glucose is not limited thereto, and glucose commonly used in the art may be used.

[Reaction Formula I]

glucose glucaric acid potassium salt

Figure 2:
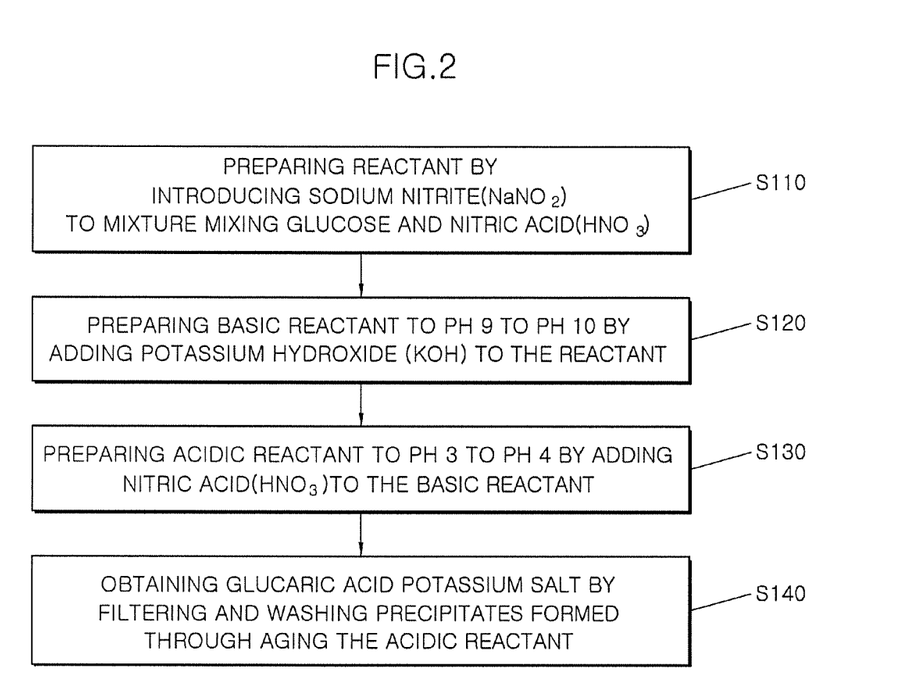
FIG. 2 shows a detailed flow chart of step (a) (i.e. S100) in a method for manufacturing adipic acid of the present invention.

Specifically, as shown in FIG. 2, S100 may be carried out through processes of preparing a reactant by introducing sodium nitrite (NaNO$_2$) to a mixture mixing glucose and nitric acid (HNO$_3$) (S110), preparing a basic reactant having a pH value in a range from about 9 to 10 by adding potassium hydroxide (KOH) to the reactant (S120), preparing an acidic reactant having a pH value from about 3 to 4 by adding nitric acid (HNO$_3$) to the basic reactant (S130) and obtaining a glucaric acid potassium salt by filtering and washing precipitates formed through aging the acidic reactant.

As one embodiment, S110 prepares a reactant by preparing a mixture through mixing about 10 to 15 g of glucose to 13 ml of nitric acid (HNO$_3$) in 70% concentration, and adding about 10 to 20 mg of sodium nitrite (NaNO$_2$) to the mixture. Herein, the reaction temperature condition for preparing the reactant is in a range from 40° C. to 60° C.

In S110, the sodium nitrite and the glucose may be mixed in a weight ratio in a range from 1:500 to 1:1500, and may be preferably mixed in a weight ratio of 1:1000.

S120 prepares a basic reactant by cooling the reactant prepared in S110 to room temperature of 15° C. to 30° C., and then basifying the result to a pH value in a range from 9 to 10 through adding 45% potassium hydroxide (KOH).

The condition being outside the basicity range condition provided above in S120 has a disadvantage in that the glucaric acid potassium salt is not properly formed, and therefore, the basicity condition provided above is preferably satisfied.

After that, an acidic reactant is prepared by acidifying the basic reactant prepared in S120 again to a pH value from 3 to 4 through adding 70% nitric acid (HNO$_3$) (S130).

Then, when the prepared acidic reactant is aged for 12 hours at room temperature, formed solid particles precipitate as precipitates, and these precipitates are filtered and washed with methanol to prepare a glucaric acid potassium salt with high purity (S140).

The pH concentration in the preparing of a basic reactant (S120) and the preparing of an acidic reactant (S130) may be checked through a pH paper, however, the method is not limited thereto, and pH measuring methods commonly used in the art may be used.

Figure 3:
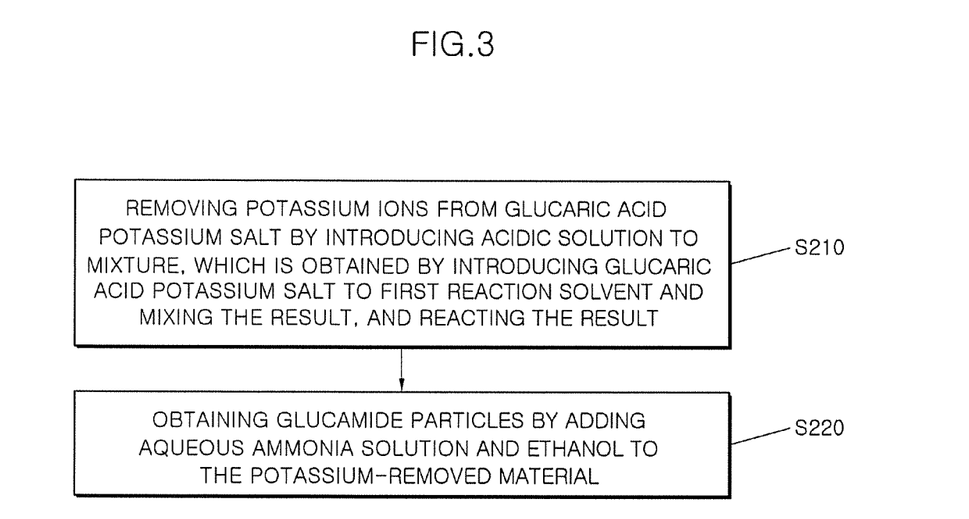
FIG. 3 shows a detailed flow chart of step (b) (i.e. S200) in a method for manufacturing adipic acid of the present invention.

As shown in FIG. 3, the preparing of glucamide from the glucaric acid potassium salt prepared in S100 (S200) may be carried out through processes of removing potassium from the glucaric acid potassium salt by introducing an acidic solution to a mixture, which is obtained by introducing the glucaric acid potassium salt to a first reaction solvent and mixing the result, and then reacting the result (S210), and obtaining glucamide particles by adding an aqueous ammonia solution and ethanol to the potassium-removed material (S220).

Specifically, in S210, 1.24 g (5 mmol) of the glucaric acid potassium salt is introduced to methanol used as a first reaction solvent, and the result is mixed. The first reaction solvent used herein is alcohols, and any one or more selected from the group consisting of primary alcohols and secondary alcohols may be used, however, the methanol provided above is the most suitable.

After that, approximately 0.3 ml to 1.0 ml of sulfuric acid (H$_2$SO$_4$) is slowly added to the mixture as an acidic solution. Herein, in addition to the sulfuric acid, para-toluene sulfonic acid may also be used as the acidic solution.

The acidic solution added in S210 functions to detach potassium (K) ions of the glucaric acid potassium salt, and therefore, the reaction time in this process is maintained for a time in a range from 12 hours to 24 hours so that the potassium ions are properly removed, and a salt-formed potassium sulfate (K$_2$SO$_4$) precipitated when cooling the result at room temperature is filtered and removed.

In the collecting of glucamide particles (S220) as the next process, the methanol used as the first reaction solvent of the potassium (K⁺ ion)-removed material obtained in S210 is all removed through evaporation, and then, while a reactor holding the methanol-evaporated reactant is kept in a low temperature bath of 0° C. to maintain the low temperature, 10 ml of an aqueous ammonia (NH₃) solution was added to the reactant. The result is mixed for a time in a range from 2 hours to 4 hours, and after further introducing 150 ml of ethanol thereto, the result is mixed for 10 minutes and then left unattended for 10 minutes to produce a particulate glucamide material.

As the aqueous ammonia solution, those dissolving ammonia (NH₃) in water in a concentration in a range from 25% by weight to 28% by weight are preferably used.

As described above and shown in the following Reaction Formula 2 as one embodiment, in S200, glucamide may be prepared from the glucaric acid potassium salt by removing potassium (K⁺ ions) of the glucaric acid potassium salt by slowly adding 0.3 ml of sulfuric acid (H₂SO₄) to a mixture, which is obtained by adding 1.24 g (5 mmol) of the glucaric acid potassium salt to 150 ml of methanol and mixing the result, and then reacting the result for 12 hours; removing all the methanol from such a potassium (K⁺ ion)-removed reactant through evaporation; and then, while a reactor holding the methanol-evaporated reactant is kept in a low temperature bath of 0° C. to maintain the low temperature, adding 10 ml of an aqueous ammonia (NH₃) solution thereto and mixing the result for 2 hours; and, after further introducing 150 ml of ethanol thereto, mixing the result for 10 minutes and leaving the result for 10 minutes.

[Reaction Formula 2]

Figure 4:
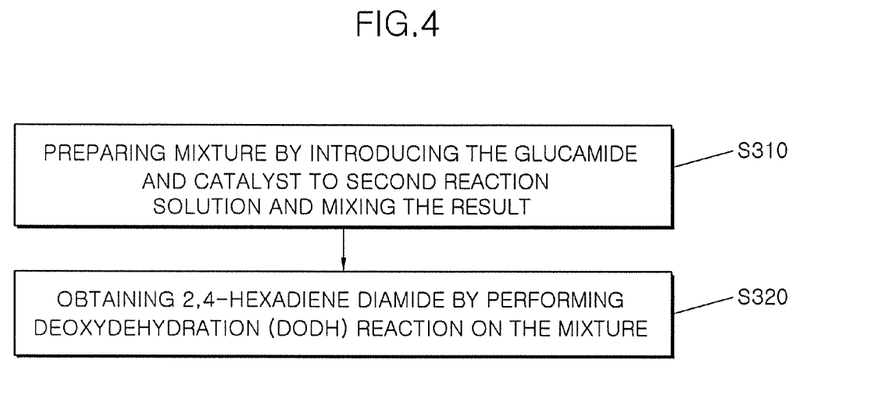
FIG. 4 shows a detailed flow chart of step (c) (i.e. S300) in a method for manufacturing adipic acid of the present invention.

As shown in the following Reaction Formula 3, S300 may prepare 2,4-hexadiene diamide from the glucamide prepared through S200 by performing a deoxydehydration (DODH) reaction, and specifically, as shown in FIG. 4, includes preparing a mixture by adding the glucamide and a catalyst to a second reaction solvent (S310) and obtaining 2,4-hexadiene diamide by performing a deoxydehydration (DODH) reaction on the mixture (S320).

[Reaction Formula 3]

As the second reaction solvent, any one or more selected from the group consisting of primary alcohols and secondary alcohols having 1 to 10 carbon atoms may be used, and preferably, butanol, 3-pentanol or 1-heptanol may be used.

As the catalyst, one or more selected from the group consisting of ammonium perrhenate, rhenium oxide (Re₂O₇) and $L_xReO_y$ (herein, L=amine, halogen, phenylsilyl, phosphine, alkoxy having 1 to 10 carbon atoms, alkyl having 1 to 10 carbon atoms or COOR (herein, R is alkyl having 1 to 10 carbon atoms), x and y are each independently an integer of 1 to 3, and x+y=7) may be used, and ammonium perrhenate may be preferably used.

Specifically, S310 prepares a mixture by mixing 104 mg (0.5 mmol) of the glucamide, 67 mg (0.25 mmol) of ammonium perrhenate as a catalyst, and 40 ml of butanol as a second reaction solvent.

Next, 2,4-hexadiene diamide is prepared by performing a deoxydehydration (DODH) reaction through the prepared mixture while being stirred under reflux using a dean-stark method for 12 hours to 24 hours while maintaining a reaction temperature in a range from 120° C. to 150° C. (S320).

Herein, the reaction temperature of lower than 120° C. has a problem of reducing a preparation yield of 2,4-hexadiene diamide, and when the temperature is higher than 150° C., byproducts increase causing a problem of reducing separation efficiency of prepared 2,4-hexadiene diamide, a product. In addition thereto, excessively high energy consumption is required at the high reaction temperature, which is not suitable for the manufacturing process.

When the reaction time is 12 hours or less, the deoxydehydration (DODH) reaction is not properly performed decreasing a preparation yield of 2,4-hexadiene diamide, a target material, and when the reaction time is greater than 24 hours, the total process time increases without changing the preparation yield of 2,4-hexadiene diamide, and therefore, the reaction is preferably performed within the temperature and the process time ranges provided above.

Through the process of obtaining 2,4-hexadiene diamide by performing a deoxydehydration (DODH) reaction as above (S320), 2,4-hexadiene diamide is produced in butanol, the second reaction solution. Accordingly, 2,4-hexadiene diamide, a target material, is collected and obtained after completing the deoxydehydration (DODH) reaction and then evaporating all the butanol, the reaction solvent.

S400 is preparing adipamide by performing a hydrogenation reaction on the 2,4-hexadiene diamide prepared in S300, and, as in the following Reaction Formula 4, prepares adipamide through changing double bonds in the 2,4-hexadiene diamide molecular structure to single bonds by inducing a hydrogenation reaction on the 2,4

[Reaction Formula 4]

-hexadiene diamide using hydrogen gas and a hydrogenation catalyst.

Specifically, the preparing of adipamide (S400) introduces hydrogen gas as a hydrogen raw material with a pressure of 1 bars to 30 bar to a reactor, and introduces the 2,4-hexadiene diamide and a hydrogenation catalyst in a weight ratio in a range from 1:0.05 to 1:0.3 to perform a hydrogenation reaction at a temperature in a range from 50° C. to 70° C.

The hydrogenation catalyst is a catalyst for converting double bonds of the 2,4-hexadiene diamide to single bonds and may use a precious metal catalyst, and specifically, any one or more selected from among aluminum, silica, a platinum catalyst supported on a carbon carrier (Pt/C) and a palladium catalyst supported on a carbon carrier (Pd/C) may be used.

Herein, in the platinum catalyst supported on a carbon carrier (Pt/C) and the palladium catalyst supported on a carbon carrier (Pd/C), support ratios of the platinum and the palladium, precious metals, with respect to the carbon carrier is preferably 10% by weight.

The reaction temperature of the hydrogenation reaction being lower than 50° C. in S400 has a problem of reducing hydrogenation reactivity, and when the temperature is greater than 70° C., byproducts increase leading to a problem in the preparation efficiency, and therefore, the reaction is preferably performed within the temperature range of 50° C. to 70° C. provided above.

As a next step, S500 prepares adipic acid as in the following Reaction Formula 5 by performing a hydrolysis reaction on the adipamide prepared through the hydrogenation reaction in S400 in an aqueous solution under acidic condition.

[Reaction Formula 5]

adipic acid

Figure 5:
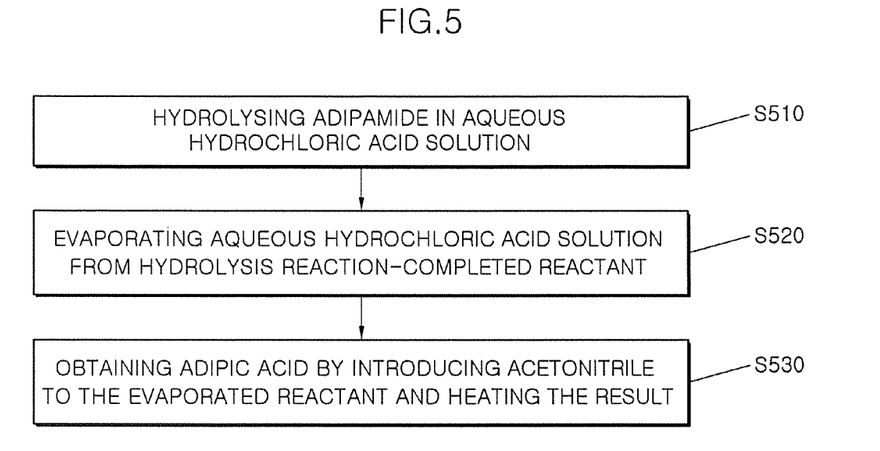
FIG. 5 shows a detailed flow chart of step (e) (i.e. S500) in a method for manufacturing adipic acid of the present invention.

As shown in FIG. 5, S500 may be carried out through processes of hydrolyzing the adipamide in an aqueous hydrochloric acid solution as an aqueous solution under acidic condition (S510), evaporating the aqueous hydrochloric acid solution from the hydrolysis reaction-completed reactant (S520), and obtaining adipic acid by introducing acetonitrile to the evaporated reactant and heating the result (S530).

Specifically, the hydrolyzing of the adipamide (S510) is carried out by introducing the adipamide and an aqueous hydrochloric acid solution to a reactor, heating the result to a temperature of 100° C., and performing a hydrolysis reaction.

Herein, the aqueous hydrochloric acid solution used herein is a mixture mixing hydrochloric acid and water in a weight ratio in a range from 1:0.05 to 1:0.3, and an aqueous hydrochloric acid solution dissolved in a concentration in a range from 20% by weight to 35% by weight, and more preferably in a concentration of 35% by weight may be used.

When the mixing ratio of the hydrochloric acid and the water is outside the above-mentioned range, the hydrolysis reaction may not be properly performed, which may cause a problem of reducing a preparation yield of adipic acid, a final target material.

Through S510, the used aqueous hydrochloric acid solution is evaporated to the maximum and removed from the hydrolysis reaction-completed reactant (S520), then acetonitrile is added to the aqueous hydrochloric acid solution-removed reactant, the result is heated again to a temperature of 100° C. and then cooled to room temperature of 15° C. to 30° C. to obtain white adipic acid particles, a final target material (S530).

Figure 6:
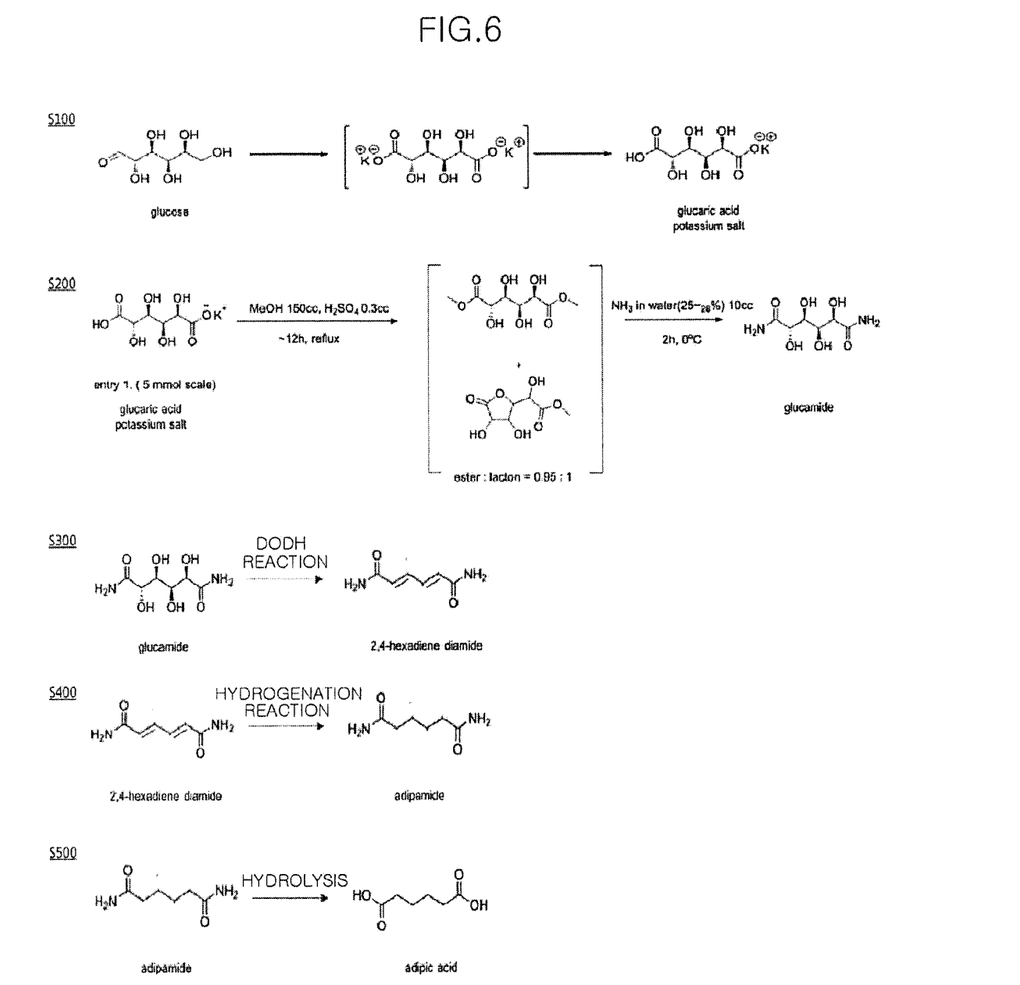
FIG. 6 illustrates a formula of a reaction manufacturing adipic acid from glucose consecutively according to one embodiment of the present invention.

Such a method for manufacturing adipic acid according to one embodiment of the present invention prepares, as shown in the reaction formula of FIG. 6, adipic acid, a final target material, from glucose consecutively through a glucaric acid potassium salt, glucamide, 2,4-hexadiene diamide and adipamide, intermediate materials.

Hereinafter, the present invention will be described in more detail with reference to examples, comparative examples and experimental examples. However, the following examples, comparative examples and experimental examples are for illustrative purposes only, and the present invention may be diversely modified and changed without being limited to the following examples, comparative examples and experimental examples.

The following Table 1 shows content ranges and reaction conditions of materials provided in step (a) (S100) to step (e) (S500), and, based on the method for manufacturing adipic acid of the present invention such as temperature and time, summarizes and shows syntheses of adipic acid together with reaction conditions in Example 1 to Example 4 and Comparative Example 1 to Comparative Example 7.

TABLE 1

| Category | Example 1 | Example 2 | Example 3 | Example 4 | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|---|---|---|
| Step (a) | Nitric Acid, KOH | Nitric Acid, KOH | Nitric Acid, KOH | Nitric Acid, KOH | Nitric Acid | Nitric Acid, KOH | Nitric Acid, KOH | Nitric Acid, KOH | Nitric Acid, KOH | Nitric Acid, KOH | Nitric Acid, KOH |
| Step (b) | Sulfuric Acid, Ammonia Water | Sulfuric Acid, Ammonia Water | Sulfuic Acid, Ammonia Water | Sulfuric Acid, Ammonia Water | Sulfuric Acid, Ammonia Water | Sulfuric Acid | Sulfuric Acid, Ammonia Water | Sulfuric Acid | Sulfuric Acid, Ammonia Water | Sulfuric Acid, Ammonia Water | Sulfuric Acid, Ammonia Water |
| Step (c) | APR | APR | APR | APR | APR | APR | APR | Ni Catalyst | APR | APR | APR |
| Reaction Temperature/ °C. | 125 | 130 | 135 | 140 | 125 | 125 | 125 | 125 | 125 | 50 | 50 |
| Step (d) | 10 wt % Pd/C, $H_2$ 30 bar, 24 hr. | 10 wt % Pd/C, $H_2$ 30 bar, 18 hr. | 10 wt % Pd/C, $H_2$ 30 bar, 16 hr. | 10 wt % Pd/C, $H_2$ 30 bar, 12 hr. | 10 wt % Pd/C, $H_2$ 30 bar, 24 hr. | 10 wt % Pd/C, $H_2$ 30 bar, 24 hr. | 10 wt % Pd/C, $H_2$ 30 bar, 24 hr. | $H_2$ 30 bar, 12 hr. | 10 wt % Pd/C, $H_2$ 30 bar, 24 hr. | 10 wt % Pd/C, $H_2$ 30 bar, 24 hr. | 10 wt % Pd/C, $H_2$ 30 bar, 24 hr. |
| Step (e) | 35 wt % Hydrochloric Acid, 100° C. | 25 wt % Hydrochloric Acid, 100° C. | 20 wt % Hydrochloric Acid, 100° C. | 20 wt % Hydrochloric Acid, 100° C. | 35 wt % Hydrochloric Acid, 100° C. | 35 wt % Hydrochloric Acid, 100° C. | 35 wt % Hydrochloric Acid, 100° C. | 35 wt % Hydrochloric Acid, 100° C. | 100% Water, 100° C. | 35 wt % Hydrochloric Acid, 100° C. | 35 wt % Hydrochloric Acid, 50° C. |
| Synthesis of Adipic Acid | Yes | Yes | Yes | Yes | No | No | No | No | No | No | No |

Step (a): treatment with nitric acid and potassium hydroxide (KOH) in preparing glucaric acid potassium salt from glucose (Sigma-Aldrich US)
Step (b): sulfuric acid and aqueous ammonia solution (concentration: 25% by weight to 28% by weight) treatment in preparing glucamide from glucaric acid potassium salt
Step (c): type of catalyst used in preparing 2,4-hexadiene diamide through DODH reaction of glucamide; ammonium perrhenate (APR), Reaction temperature: DODH reaction temperature condition
Step (d): catalyst used, hydrogen gas pressure, reaction time condition in preparing adipamide from 2,4-hexadiene diamide through a hydrogenation reaction
Step (e): concentration of aqueous hydrochloric acid (Daejung Chemicals & Metals) solution used and reaction temperature condition in preparing adipic acid through hydrolysis of adipamide As shown in Table 1, Comparative Examples 1 to 7 are cases in which the reaction conditions provided in each step of the method for manufacturing adipic acid of the present invention are not satisfied, and the results may be specifically reviewed as follows.

First, when a basification reaction using potassium hydroxide (KOH) was not progressed in the step (a) preparing a glucaric acid potassium salt from glucose as in Comparative Example 1, salt formation was not proper and the glucaric acid potassium salt was not properly formed, and as a result, adipic acid was not synthesized.

Comparative Example 2 is a case in which aqueous ammonia solution treatment was not properly carried out in the step (b) preparing glucamide from the glucaric acid potassium salt, and when aqueous ammonia solution treatment was not carried out after removing potassium (i.e. $K^+$ ion) from the glucaric acid potassium salt, glucamide particles were not formed, and as a result, adipic acid was not synthesized.

As in Comparative Example 3, when using a nickel (Ni) catalyst instead of ammonium perrhenate (APR) as the catalyst used in the step (c) preparing 2,4-hexadiene diamide from the glucamide through performing a deoxydehydration (DODH) reaction, the deoxydehydration (DODH) was not properly performed, and 2,4-hexadiene diamide was not properly formed, and as a result, adipic acid was not synthesized.

As in Comparative Example 4, when a hydrogenation catalyst was not used in the step (d) preparing adipamide through performing a hydrogenation reaction on the 2,4-hexadiene diamide, the hydrogenation reaction was not properly performed and double bonds in the 2,4-hexadiene diamide molecular structure were not properly converted to single bonds, and as a result, adipic acid was not synthesized.

Comparative Example 5 is when a hydrolysis reaction was performed under a condition that is not acidic in the step (e) preparing adipic acid through a hydrolysis reaction on the adipamide, and as a result, it was seen that adipic acid was not synthesized.

Meanwhile, Comparative Example 6 and Comparative Example 7 are cases in which the reaction temperature condition is outside the range provided in the method for manufacturing adipic acid of the present invention, and in Comparative Example 6, the deoxydehydration (DODH) reaction was not properly performed when the temperature condition in the deoxydehydration (DODH) reaction of the step (c) was 50° C. that was outside the provided 120° C. to 150° C., and as a result, it was seen that adipic acid was not synthesized.

In Comparative Example 7, the hydrolysis reaction was not properly performed when the heating condition in the hydrolysis reaction of the step (e) was 50° C. instead of 100° C., and as a result, it was seen that adipic acid was not synthesized.

In Experimental Example 1, nuclear magnetic resonance (NMR) analyses were performed on the samples manufactured in Examples 1 to 4 in order to identify their components. Nuclear magnetic resonance spectra (NMR spectra) were analyzed using Bruker AVIII400 instrument, and measurements were made after dissolving each of the samples in $CDCl_3$ and dimethyl sulfoxide (DMSO) including trimethylsilane (TMS) as an internal standard ($^1H$ at 400 MHz, $^{13}C$ at 100 MHz).

Figure 7:
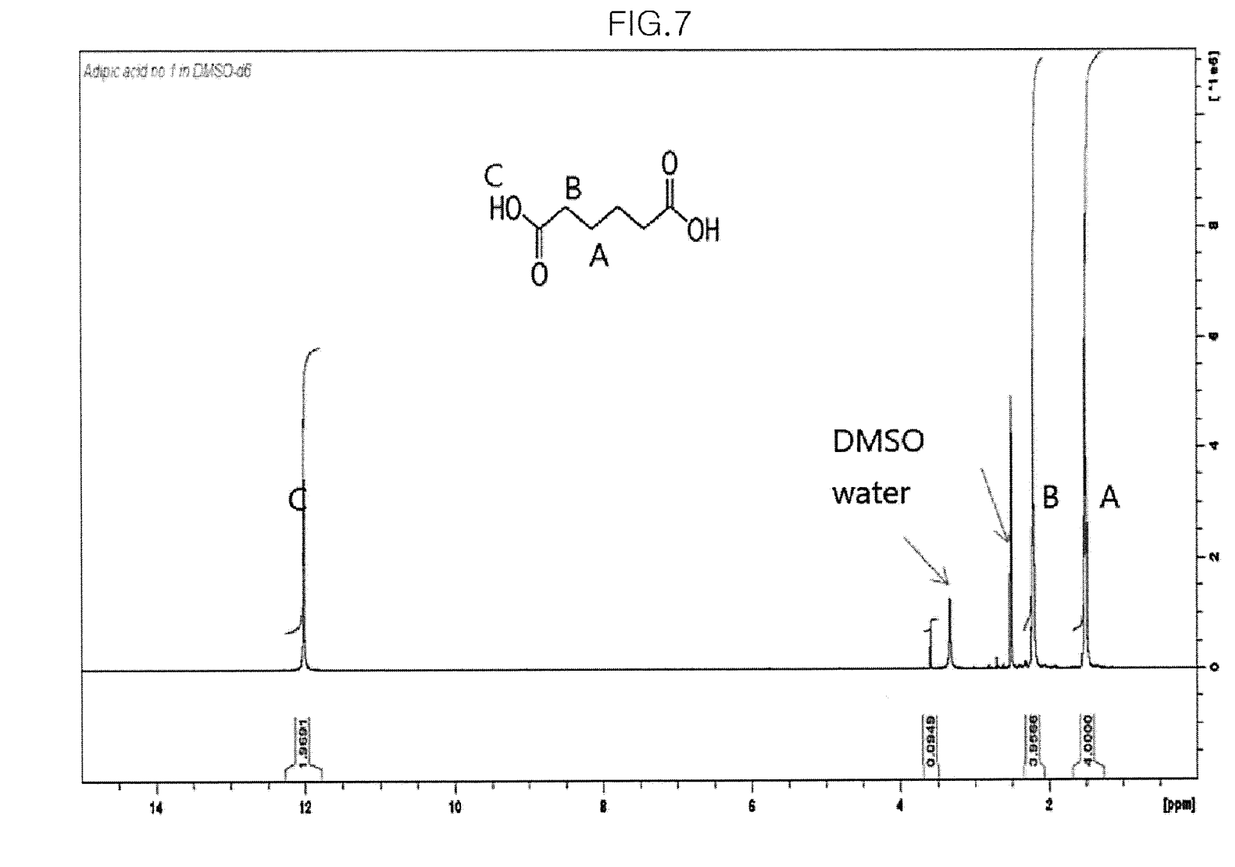
FIG. 7 shows nuclear magnetic resonance NMR analysis data of adipic acid manufactured according to one embodiment of the present invention.

Such nuclear magnetic resonance analysis results identified that, as shown in FIG. 7, adipic acid, a target material, was manufactured as a result of nuclear magnetic resonance analysis data obtained from analyzing the samples of Examples 1 to 4 of the present invention.

Accordingly, an excellent dibutyl muconate yield obtained in the examples of the present invention also affected adipic acid manufacturing afterward, and an effect of enhancing an adipic acid yield was obtained as well.

Existing synthesis processes of adipic acid from petrochemical materials generally have problems in that very strong and toxic chemical products are used or yields are very low, however, according to such a manufacturing method of the present invention, adipic acid is prepared from glucose derived from biomass such as plant resources, an environmental-friendly material, which raises potential that adipic acid may be manufactured in high yields at low costs through a process environmental-friendly and far simpler than existing production methods, and as a result, the manufacturing method of the present invention has a great industrial ripple effect as a technology utilizing adipic acid as a raw material of nylon 66 used as a material of automotive components.

Unlike existing methods for manufacturing adipic acid dependent on petrochemical materials, the method for manufacturing adipic acid of the present invention as described above manufactures adipic acid from biomass such as plant resources, an environmental-friendly material, and therefore, is environmental-friendly.

In addition, an effect of manufacturing adipic acid in high efficiency at low costs is obtained through a simple process compared to existing petrochemical or biotechnological production methods, and therefore, the adipic acid may be utilized as a raw material of nylon 66 used as a material of automotive components in the future.

What is claimed is:

1. A method for preparing bio adipic acid comprising steps of:
   (a) preparing a glucaric acid potassium salt by mixing and reacting glucose, nitric acid ($HNO_3$), sodium nitrite ($NaNO_2$) and potassium hydroxide (KOH);
   (b) preparing glucamide from the glucaric acid potassium salt prepared in the step (a);
   (c) preparing 2,4-hexadiene diamide by performing a deoxydehydration reaction on the glucamide prepared in the step (b);
   (d) preparing adipamide by introducing the 2,4-hexadiene diamide prepared in the step (c), hydrogen and a hydrogenation catalyst to a reactor and performing a hydrogenation reaction; and
   (e) preparing the bio adipic acid by introducing the adipamide prepared in the step (d) and an aqueous hydrochloric acid solution to a reactor and then performing a hydrolysis reaction at a specific temperature.

2. The method for preparing the bio adipic acid of claim 1, wherein the step (a) further includes steps of:
   preparing a reactant by introducing and reacting the sodium nitrite ($NaNO_2$) to a mixture of glucose and nitric acid ($HNO_3$) at a specific temperature;
   preparing a basic reactant having a pH value in a range from 9 to 10 by adding the potassium hydroxide (KOH) to the reactant;
   preparing an acidic reactant having a pH value in a range from 3 to 4 by adding the nitric acid ($HNO_3$) to the basic reactant; and
   collecting the glucaric acid potassium salt by filtering and washing precipitates formed through aging the acidic reactant.

3. The method for preparing the bio adipic acid of claim 2, wherein the preparing of the reactant is carried out at a reaction temperature of 40° C. to 60° C.

4. The method for preparing the bio adipic acid of claim 1, wherein, in the step (a), the glucose and the sodium nitrite are mixed in a weight ratio in a range from 1:500 to 1:1500.

5. The method for preparing the bio adipic acid of claim 1, wherein the step (b) includes steps of:
   removing potassium from the glucaric acid potassium salt by
     introducing an acidic solution to a mixture obtained by introducing and mixing the glucaric acid potassium salt to a first reaction solvent, and
     then reacting the acidic solution and the mixture for a specific period of time; and
   collecting particles of the glucamide precipitated by
     adding an aqueous ammonia solution to the glucaric acid potassium salt with the potassium removed,
     mixing the glucaric acid potassium salt with the potassium removed and added with the aqueous ammonia solution for a specific period of time, and then
     adding ethanol thereto.

6. The method for preparing the bio adipic acid of claim 5, wherein the first reaction solvent is any one or more selected from the group consisting of primary alcohols and secondary alcohols having 1 to 10 carbon atoms.

7. The method for preparing the bio adipic acid of claim 5, wherein the acidic solution is sulfuric acid ($H_2SO_4$) or para-toluene sulfonic acid.

8. The method for preparing the bio adipic acid of claim 5, wherein the removing of potassium is carried out for a reaction time in a range from 12 hours to 24 hours.

9. The method for preparing the bio adipic acid of claim 5, wherein a concentration of the aqueous ammonia solution is in a range from 25% by weight to 28% by weight.

10. The method for preparing the bio adipic acid of claim 1, wherein the step (c) includes steps of:
    preparing a mixture by introducing and mixing the glucamide and a catalyst to a second reaction solvent; and
    collecting the 2,4-hexadiene diamide formed by carrying out a deoxydehydration (DODH) reaction through the mixture while being stirred under reflux for a time in a range from 12 hours to 24 hours at a temperature in a range from 120° C. to 150° C.

11. The method for preparing the bio adipic acid of claim 10, wherein the second reaction solvent is any one or more selected from the group consisting of primary alcohols and secondary alcohols having 1 to 10 carbon atoms.

12. The method for preparing the bio adipic acid of claim 10, wherein the catalyst is one or more selected from the group consisting of ammonium perrhenate, rhenium oxide ($Re_2O_7$) and $L_xReO_y$ (herein, L=amine, halogen, phenylsilyl, phosphine, alkoxy having 1 to 10 carbon atoms, alkyl having 1 to 10 carbon atoms or COOR (herein, R is alkyl having 1 to 10 carbon atoms), x and y are each independently an integer in a range from 1 to 3, and satisfies x+y=7).

13. The method for preparing the bio adipic acid of claim 1, wherein the step (d) is performed by introducing the 2,4-hexadiene diamide and the hydrogenation catalyst to the reactor in a weight ratio in a range from 1:0.05 to 0.3.

14. The method for preparing the bio adipic acid of claim 1, wherein the hydrogen is introduced with a pressure in a range from 1 bar to 30 bar.

15. The method for preparing the bio adipic acid of claim 1, wherein the hydrogenation catalyst is any one selected from among aluminum, silica, a platinum catalyst supported on a carbon carrier (Pt/C), and a palladium catalyst supported on a carbon carrier (Pd/C).

16. The method for preparing the bio adipic acid of claim 1, wherein the step (d) carries out the hydrogenation reaction at a temperature in a range from 50° C. to 70° C.

17. The method for preparing the bio adipic acid of claim 1, wherein, in the step (e), the aqueous hydrochloric acid solution is formed by mixing hydrochloric acid and water in a weight ratio in a range from 1:0.05 to 1:0.3.

18. The method for preparing the bio adipic acid of claim 1, wherein the step (e) further includes steps of:
- evaporating hydrochloric acid and water from a reactant formed after completing the hydrolysis reaction, forming an evaporated reactant; and
- obtaining the bio adipic acid by mixing and heating acetonitrile with the evaporated reactant.

\* \* \* \* \*